United States Patent [19]

Cullinan

[11] 4,012,390
[45] Mar. 15, 1977

[54] VINBLASTINOIC ACID

[75] Inventor: George J. Cullinan, Trafalgar, Ind.

[73] Assignee: Eli Lilly and Company, Indianapolis, Ind.

[22] Filed: Oct. 16, 1974

[21] Appl. No.: 515,134

[52] U.S. Cl. .......................................... 260/287 B
[51] Int. Cl.² ...................................... C07D 519/04
[58] Field of Search ................................ 260/287 B

[56] References Cited

UNITED STATES PATENTS

| 3,352,868 | 4/1964 | Neuss et al. | 260/287 |
| 3,387,001 | 6/1968 | Hargrove | 260/287 |
| 3,392,173 | 7/1968 | Hargrove | 260/287 |

OTHER PUBLICATIONS

Hargrove, *Lloydia*, 1964, pp. 340–345, vol. 27.
Cheng et al., "J. of Pharm. Sci.," 1970, pp. 1630–1632.

*Primary Examiner*—Donald G. Daus
*Assistant Examiner*—David E. Wheeler
*Attorney, Agent, or Firm*—James L. Rowe; Everet F. Smith

[57] ABSTRACT

Vinblastine, vincristine and leurosidine are converted to 3-carboxylic acids and 4-desacetyl-3-carboxylic acids, useful as intermediates to prepare aliphatic esters thereof.

1 Claim, No Drawings

VINBLASTINOIC ACID

BACKGROUND OF THE INVENTION

Several naturally-occurring alkaloids obtainable from *Vinca rosea* have been found active in the treatment of experimental malignancies in animals. Among these are leurosine (U.S. Pat. No. 3,370,057), vincaleukoblastine (vinblastine) to be referred to hereinafter as VLB (U.S. Pat. No. 3,097,137), leurosidine (vinrosidine) and leurocristine (VCR or vincristine) (both in U.S. Pat. No. 3,205,220). Two of these alkaloids, VLB and leurocristine, are now marketed as drugs for the treatment of malignancies, particularly the leukemias and related diseases in humans. Of these marketed compounds, leurocristine is a most active and useful agent in the treatment of leukemias but is also the least abundant of the anti-neoplastic alkaloids of *Vinca rosea*.

Chemical modification of the *Vinca* alkaloids has been rather limited. In the first place, the molecular structures involved are extremely complex and chemical reactions which affect a specific function of the molecule are difficult to develop. Secondly, alkaloids lacking desirable chemotherapeutic properties have been recovered from *Vinca rosea* fractions, and a determination of their structures has led to the conclusion that these compounds are closely related to the active alkaloids. Thus, anti-neoplastic activity seems to be limited to very specific structures, and the chance of obtaining more active drugs by modification of these structures would seem to be correspondingly slight. Among the successful modifications of physiologically-active alkaloids has been the preparation of dihydro VLB (U.S. Pat. No. 3,352,868) and the replacement of the acetyl group at C-4 (carbon no. 4 of the VLB ring system-see the numbered structure below) with higher alkanoyl group or with unrelated acyl groups. (See U.S. Pat. No. 3,392,173.) Several of these derivatives are capable of prolonging the life of mice inoculated with P1534 leukemia. One of the derivatives in which a chloracetyl group replaced the C-4 acetyl group of VLB was also a useful intermediate for the preparation of structurally modified VLB compounds in which an N,N-dialkylglycl group replaced the C-4 acetyl group of VLB (see U.S. Pat. No. 3,387,001). An intermediate compound, namely 4-desacetyl VLB, was produced during the chemical reactions leading to these latter derivatives. This intermediate, in which the C-4 acyl group was lacking, leaving an unesterified hydroxy group, has been reported to be a toxic material having little in vivo chemotherapeutic activity against the P1534 murine leukemia system by Hargrove, *Lloydia*, 27, 340 (1964). Desacetylvinblastinoic acid-vinblastine with the C-3 methyl ester group replaced by a carboxyl group and having a hydroxy at C-4 in place of acetoxy-is also disclosed in that article.

Neuss et al., *Tetrahedron Letters*, 1968, 783–7, disclosed the formation of deoxy vinblastine which lacks a 4'-hydroxy group and its derivates lacking a carbomethoxy group at C-18'.

Novel C-3 amides of vinblastine were disclosed by Sweeney, Cullinan, Poore and Gerzon at 65th Annual Meeting of the American Association for Cancer Research, held at Houston, Texas, March 27–30, 1974 (Proceedings, Abstract 146).

SUMMARY OF THE INVENTION

This invention provides compounds of the formula:

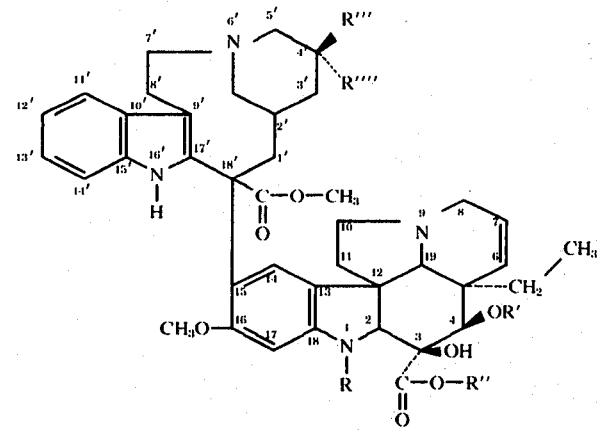

wherein
R is $CH_3$, CH=O or H,
R' is H or acetyl,
R" is H, ($C_2$–$C_5$) alkyl, mono or dihydroxy ($C_2$–$C_5$) alkyl, monohalo ($C_2$–$C_5$) alkyl, mono($C_2$–$C_4$) alkanoyloxy ($C_2$–$C_5$) alkyl, crotyl, methallyl, allyl, propargyl or 2-butyn-4-ol;
one of R''' and R'''' is hydroxyl and the other is ethyl; with the proviso that only one of R' and R" can be hydrogen when R is $CH_3$;
and pharmaceutically acceptable salts thereof formed with non-toxic acids.

In formula I above, compound in which R is $CH_3$ are members of the vinblastine or leurosidine series, compounds in which R is CHO are members of the vincristine series, and compounds in which R is H are members of the desformyl vincristine, or alternatively, the desmethyl vinblastine or desmethyl leurosidine series. Leurosidine and vinblastine are stereoisomers, varying in the orientation of the ethyl and hydroxyl groups attached at C-4'. For vinblastine, R''' is OH (β) and R'''' is ethyl (α). The reverse is true of leurosidine, R''' being ethyl and R'''' hydroxyl. Vincristine has the same orientation of hydroxyl and ethyl at C-4' as vinblastine. Compounds in which R' is hydrogen are referred to as desacetyl compounds as, for example, desacetyl vinblastine, desacetyl leurosidine or desacetyl vincristine. The novel compound of this invention in which R" is H, R' is acetyl, R''' is OH, R'''' is $C_2H_5$ and R is $CH_3$ has been named "vinblastinoic acid"; where R" is H, R' is acetyl, R''' is OH R'''' is C$_2$H$_5$ and R is formyl, "vincristinoic acid"; and where R" is H, R' is acetyl, R''' is C$_2$H$_5$, R'''' is OH and R is CH$_3$, leurosidinoic acid.

The novel esters of this invention in which R" is (C$_2$–C$_5$) alkyl, mono or dihydroxy (C$_2$–C$_5$) alkyl, monohoalo (C$_2$–C$_5$) alkyl, mono (C$_2$–C$_4$) alkanoyloxy (C$_2$–C$_5$) alkyl, crotyl, methallyl, allyl, propargyl or 2-butyn-1-ol, one of R''' and R'''' is hydroxyl and the other is ethyl, can be named 3-desmethyl-3-ethyl [or 3-propyl, 3-(2-chlorobutyl), or 3-(2-hydroxypentyl)-]vinblastine or leurosidine or vincristine or 4-desacetyl vinblastine, etc., but preferably as ethyl vinblastinoate or propyl vincristinoate or butyl 4-desacetyl vinblastionate or ethyl 4-desacetyl leurosidinoate, etc.

In the above formula, when R" is (C$_2$–C$_5$) alkyl, it can be ethyl, n-propyl, isopropyl, n-butyl, isobutyl, sec-butyl, 1-pentyl, isopentyl, 2-pentyl, 3-pentyl, 3-methyl-2-butyl, neopentyl and the like. Mono and dihydroxy substituted (C$_2$–C$_5$) alkyl which R" represents include 2-hydroxyethyl, 2,3-dihydroxypropyl, 2-hydroxy-2-methylethyl, 2-hydroxy-1-methylethyl, 2-hydroxy-2,2-dimethylethyl, 2-hydroxy-1,1-dimethylethyl, 2-hydroxybutyl, 3-hydroxypropyl, 4-hydroxybutyl, 5-hydroxypentyl, 2,3-dihydroxy-2-methylpropyl, and the like groups. Halo (C$_2$–C$_5$) alkyl groups which R" represents include 2-chloroethyl, 2-bromoethyl, 2-chloropropyl, 2-bromobutyl, 3-chloropropyl, 2-chloropentyl, 2-bromo-3-methylbutyl, 4-bromobutyl and the like. Mono (C$_2$–C$_4$) alkanoyloxy (C$_2$–C$_5$) alkyl groups which R" represents include 2-acetoxy-1-ethyl, 2-propionoxy-1-propyl, 3-acetoxy-1-propyl, 2-isobutyloxy-2-butyl, 2-acetoxy-2pentyl, 2-butyloxy-1-pentyl, 2-propionoxy-3-methyl-1-propyl, isobutyloxy-2-butyl, 2-acetoxy-2-pentyl, 2-butyloxy-1-pentyl, 2-propionoxy-3-methyl-1-pentyl and the like.

Non-toxic acids useful for forming pharmaceutically-acceptable acid addition salts of the amine bases represented by formula I above include salts derived from inorganic acids such as: hydrochloric acid, nitric acid, phosphoric acid, sulfuric acid, hydrobromic acid, hydriodic acid, nitrous acid, phosphorus acid and the like, as well as salts of non-toxic organic acids including aliphatic mono and dicarboxylates, phenyl-substituted alkanoates, hydroxy alkanoates and alkandioates, aromatic acids, aliphatic and aromatic sulfonic acids etc. Such pharmaceutically-acceptable salts thus include the sulfate, pyrosulfate, bisulfate, sulfite, bisulfite, nitrate, phosphate, monhydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, 2-hydroxybutyrate, glycollate, malate, tartrate, methanesulfonate, propanesulfonate, napthalene-1-sulfonate, napththalene-2-sulfonate and the like salts.

The compounds of this invention are prepared according to the following general procedure. Vinblastine, leurosidine or vincristine is treated with dilute base thereby hydrolyzing the ester group in the 3 position to yield a carboxylic acid group as a basic salt and also hydrolyzing the ester group in the 4 position, leaving a hydroxy group. In the case of vincristine, the formyl group at position 1 also is hydrolyzed. Thus, the products of the hydrolysis are either 4-desacetyl vinblastinoic acid, 4-desacetyl leurosidinoic acid or 1-desformyl-4-desacetyl vincristinoic acid. Acetylation in pyridine reconstitutes the 4-acetyl group to yield vinblastionic acid, leurosidinoic acid or 1-desformyl vincristinoic acid. The latter compound can be formylated with 97 percent formic acid and acetic anydride to yield vincristinoic acid. Conversely, 1-desformyl-4-desacetyl vincristinoic acid can be formylated prior to acetylation, thus forming 4-desacetyl vincristinoic acid as an intermediate. Formation of the higher esters of the above acids such as the ethyl, butyl, 2-chloroethyl, 2-acetoxypropyl and hydroxyethyl esters is carried out by treating the free acid with a solution of the desired alcohol in the presence of an acidic catalyst. The esters of vincristionic, leurosidinoic and vinblastinoic acid and of their 4-desacetyl analogs are all prepared in substantially the same fashion. The mono (C$_2$–C$_4$) alkanoyloxy (C$_2$–C$_5$) alkyl esters are generally prepared by esterification of the corresponding monohydroxy (C$_2$–C$_5$) alkyl ester using a standard acylating agent such as an acid anhydride, a mixed anhydride, an acyl chloride in the presence of an organic base, etc. In general, the esters are isolated in the form of their sulfate salts, prepared by acidifying a solution of the base to a pH in the range 2–4 with dilute sulfuric acid and then evaporating the volatile constituents to leave the sulfate salt as a residue. In general, the sulfate salts are amorphous, and the compounds are identified by their NMR spectrum and by a molecular ion spectrum carried out on the free base.

An alternative procedure exists for the preparation of 4-desacetyl vincristinoic acid and for 1-desformyl-4-desacetyl vincristinoic acid. By this procedure, 4-desacetyl vinblastine prepared by the method of Hargrove, *Lloydia*, 27, 340 (1964) is oxidized with chromic acid in acetic anhydride at low temperatures by the procedure of South African Pat. No. 72/8535 to yield a mixture of 4-desacetyl vincristine and 1-desformyl-4-desacetyl vincristine. Suprisingly, this reaction occurs without oxidizing the 4-hydroxyl to the corresponding ketone. Treatment of this mixture with dilute base produces the desired 1-desformyl-4-desacetyl vincristinoic acid.

The compounds of this invention in which R and R" are other than hydrogen have potential utility as antitumor drugs as shown by their ability to arrest cultured cells at the mitotic phase (metaphase) of the cell cycle without apparent effect on other stages of the cell cycle. Most of the known antitumor indoledihydroindole (dimeric) alkaloids from *Vinca rosea* have the ability to cause metaphase arrest, including vincaleukoblastine (VLB), vincristine and leurosine. Monomeric vinca alkaloids do not possess metaphase arrest activity and are not antimitotics. In addition, the compounds of this invention have been shown to be active against transplanted tumors in mice. Of particular interest is the high activity shown by ethyl 4-desacetyl vincristinoate sulfate against Ridgeway osteogenic sarcoma when administered for ten days by the intraperitoneal route after inoculation of the tumor at dose levels from 0.15 to 0.5 mg./kg. of mouse weight. Similar results are obtained against the Gardner lymphosarcoma. The compound also showed activity at 0.5 mg./kg. against the $C_3H$ mammary tumor at an 0.5 mg./kg. dose level. Ethyl vinblastinoate sulfate has also shown activity in the Gardner lymphosarcoma tumor system. Results obtained with ethyl 4-desacetyl vincristinoate sulfate are summarized in Table 1 below. In the table, column 1 gives the name of the compound; column 2, the transplanted tumor; column 3, the dose level or dose level range and the number of days the dosage was administered; and column 4, percent inhibition of tumor growth. (ROS is an abbreviation for Ridgeway osteogenic sarcoma; GLS for Gardner lymphosarcoma; and $C_3H$ is a mammary tumor). Higher dose levels than those listed in the table usually produced toxicity.

Table 1

| Compound | Tumor | Dose mg./kg. × days | Percent Inhibition |
|---|---|---|---|
| Ethyl 4-desacetyl vincristinoate sulfate | GLS | 0.2 × 8 | 85 |
| | | 0.25 × 8 | 87 |
| | | 0.3 × 8 | 100 |
| | | 0.4 × 8 | 100 |
| | | 0.5 × 8 | 100 |
| | ROS | 0.15 × 10 | 58 |
| | | 0.2 × 10 | 65 |
| | | 0.25 × 10 | 100 |
| | | 0.3 × 10 | 84 |
| | | 0.4 × 10 | 100 |
| | | 0.5 × 10 | 100 |
| | $C_3H$ | 0.5 × 9 | 43 |
| 2-Hydroxyethyl 4-desacetyl vinblastinoate sulfate | GLS | 0.5 × 8 | 100 |
| | | 1.0 × 8 | 91 |

In addition to their anti-tumor activity, compounds according to formula I above other than the alkyl and hydroxy alkyl esters of vincristinoic acid and of vinblastinoic acid are also useful as intermediates. For example, the 4-desacetyl compounds can be converted by acetylation to the parent vinblastinoate or vincristinoate ester. Compounds according to Formula I above in which R is hydrogen or in which R'' is hydrogen are in general not active in the mitotic inhibition test and are likewise inactive in inhibiting the growth of transplanted tumors in mice. These compounds are, however, intermediates in that the compounds in which R'' is H, the vinblastinoic, leurosidinoic and vincristinoic acids are converted by esterification to useful compounds. Similarly, the compounds in which R is hydrogen, the 1-desformyl vincristine derivatives, can be formylated to yield vincristinoic acid, another useful intermediate, or desacetyl vincristinoate esters and vincristinoate esters.

In addition to the above utility, the free acids of this invention including the desacetyl acids are useful intermediates for the preparation of radio-actively-labelled material in that they can be re-esterified with radioactive methyl alcohol according to the above procedure. Furthermore, it is possible, through the use of the desmethyl desacetyl vinblastinoic acid to methylate or formylate the compound at the N-1 nitrogen with a radioactively labelled methyl or formyl group and employ isotopically labelled methanol to re-esterify the carboxylic acid group or vice-versa, thus making possible the preparation of a doubly-labelled vincristine, leurosidine or vinblastine.

This invention is further illustrated by the following specific examples.

EXAMPLE 1

PREPARATION OF 4-DESACETYL VINBLASTINOIC ACID

Ten grams of vinblastine sulfate were converted to the corresponding free base by treatment with alkali followed by extraction of the base into methylene dichloride, drying and evaporation of the methylene dichloride. The residual vinblastine was dissolved in 200 ml. of anhydrous ethanol in a 2 l. flask fitted with a reflux condenser. The ethanol solution was heated while 956 ml. of 1 N aqueous sodium hydroxide was added from a dropping funnel along with an additional 50 ml. of anydrous ethanol. The extra ethanol was required to maintain homogeneity in the reaction mixture. The reaction mixture was refluxed for ½ hour after the sodium hydroxide had been added. Sodium chloride was then added to the warm solution, and the aqueous layer extracted with four portions of methylene dichloride. The methylene chloride extracts were combined and dried. Evaporation of the solvent in vacuo yielded 6.9 g. of an amorphous tan solid consisting of a mixture of vinblastine and of 4-desacetyl vinblastinoic acid as the sodium salt.

Two grams of impure 4-desacetyl vinblastinoic acid, as sodium salt thus prepared were dissolved in anhydrous methanol and water added to the solution to the point of turbidity. The pH of the resulting solution was adjusted to about 3.9 by the addition of 1 percent aqueous sulfuric acid. The solvents were then removed by evaporation in vacuo. The resulting solid comprising 4-desacetyl vinblastinoic acid sulfate was dissolved in an ethanol-water solvent mixture with heating, and the hot solution was filtered. Upon cooling, a light tan solid precipitated which was collected by filtration. 4-desacetyl vinblastinoic acid sulfate thus prepared had the following physical characteristics. pKa = 4.65, 6.3, 7.5 and 8.5 (in 80 percent dimethylformamide). $\lambda(EtOH,-Max) = 215$ m$\mu$ (E=12.5 × $10^3$), 267 m$\mu$. (E=4.0 × $10^3$) with shoulders at 284 and 294 and at about 314 m$\mu$.

Analysis Calc.: C, 60.55; H, 6.62; N, 6.57; Found: C, 60.80; H, 6.86; N, 6.64.

Analysis for sodium was zero.

EXAMPLE 2

PREPARATION OF VINBLASTINOIC ACID SULFATE

A suspension of 2.1 g. of 4-desacetyl vinblastinoic acid as the sodium salt was prepared in 25 ml. of anhydrous pyridine. About 25 ml. of acetic anhydride were added. The reaction vessel was fitted with a drying tube and stirred at ambient temperature for four days. Methanol was added, and the reaction mixture evaporated to dryness. This drying process was repeated several times. The residue containing vinblastinoic acid formed in the above reaction was dissolved in chloroform, and the chloroform solution extracted four times with water. The chloroform solution was then dried, and the chloroform evaporated. The resulting residue was dissolved in methanol and water added to the point of turbidity. The pH of the aqueous methanol solution was adjusted to 2.2 by the addition of 1 percent aqueous sulfuric acid. The resulting solution was evaporated to dryness using the benzene azeotrope to remove water. The residue was dissolved in isopropanol, and impurities which crystallized were separated by filtration. Evaporation of the filtrate from two such successive crystallizations yielded 200 mg. of vinblastinoic acid sulfate as a tan amorphous solid. The compound showed an enhanced band at 1740 cm.$^{-1}$ in the infrared spectrum showing an increase in ester group. The compound had pKa's at 5.2 and 7.7 (66 percent DMF).

EXAMPLE 3

PREPARATION OF ETHYL VINBLASTINOATE SULFATE 500 ml. of a saturated ethanolic hydrogen chloride solution was prepared at 0° C, 3 g. of 4-desacetyl vinblastinoic acid as the sodium salt were added. The reaction vessel was fitted with a drying tube and allowed to stand at ambient temperature in the dark for about three days. The ethanol was then evaporated, and the resulting residue dissolved in water. The aqueous layer was made basic with 14 N ammonium hydroxide. Ethyl vinblastinoate, being insoluble in the basic solution separated and was extracted with several portions of methylenedichloride. The methylene dichloride extracts were separated, combined and dried. Evaporation of the solvent yielded ethyl 4-desacetyl vinblastinoate as a tan amorphous solid. Infrared and NMR spectra of the compound were consistent with the postulated structure.

The tan solid was dissolved in 25 ml. of anhydrous pyridine which had been previously saturated with nitrogen and 25 ml. of acetic anhydride were added. The resulting reaction was placed in a sealed vessel and allowed to stand at ambient temperature in the dark for seven days. Volatile constituents were removed by evaporation in vacuo. Methanol was added and the solution evaporated to dryness again. This methanol addition and evaporation procedure was repeated several times. The residue was then chromatographed over silica gel using an ethyl acetate ethanol (2:1) solvent mixture as the eluant. Fractions containing ethyl vinblastinoate, as determined by thin layer chromatography, were collected and combined, and the solvent removed from the combined fractions by evaporation. An infrared spectrum of the resulting tan amorphous powder was consistent with the assigned structure since there was an enhanced band at 1740 cm.$^{-1}$. The compound had NMR peaks as follows: $\delta = 2.11$ (OOC$\underline{H}_3$), 1.33 (triplet for OCH$_2$C$\underline{H}_3$), 4.28 (quartet for OC$\underline{H}_2$CH$_3$), with $J_{ab}=7$ Hz. The remainder of the NMR spectrum was consistent with the postulated structure. Mass spectrum yielded a molecular ion, $m/e = 824$, in agreement with a postulated empirical formula C$_{47}$H$_{60}$N$_4$O$_9$. Ethyl vinblastinoate free base thus obtained was dissolved in methanol and water added to the point of turbidity. The pH of the solution was adjusted to about 3 with 1 percent aqueous sulfuric acid and the resulting solution evaporated to dryness using the benzene azeotrope to remove the water. Recrystallization of the residue from anhydrous ethanol yielded a cream-colored solid having pKa = 4.6, 6.0 and 7.45 (66percent DMF). The yield of ethyl vinblastinoate sulfate was 204 mg.

Following the above procedure, 4-desacetyl vinblastinoic acid sodium salt was esterified with methanol saturated with anhydrous hydrogen chloride to yield methyl 4-desacetyl vinblastinoate (4-desacetyl vinblastine). The compound was identical in all respects to an authentic sample of 4-desacetyl vinblastine prepared by hydrolysis of vinblastine.

EXAMPLE 4

PREPARATION OF n-BUTYL VINBLASTINOATE SULFATE

Following the procedure of the previous example, 473 ml. of n-butanol were saturated with anhydrous hydrogen chloride at 0° C. 3 g. of 4-desacetyl vinblastinoic acid, sodium salt, were added and the reaction mixture allowed to stand at ambient temperature in the dark for 3 days. n-Butyl 4-desacetyl vinblastinoate was isolated and purified by the procedure of the previous example. The compound was acetylated in dry pyridine as in the previous example and n-butyl vinblastinoate thus prepared obtained by chromatography. The compound had the following physical characteristics. NMR spectrum peaks $\delta$ 2.11 (OOC$\underline{H}_3$), 0.94 (multiplet for OCH$_2$CH$_2$CH$_2$C$\underline{H}_3$) = 1.1-1.8 (multiplet for OCH$_2$C$\underline{H}_2$C$\underline{H}_2$CH$_3$), 4.19 multiplet for OC$\underline{H}_2$C$_3$H$_7$). The remainder of the NMR spectrum was consistent with the postulated structure. Mass spectrum analysis yielded a molecular ion $m/e = 852$ consistent with the postulated empirical formula C$_{49}$H$_{64}$N$_4$O$_9$.

The sulfate salt of n-butyl vinblastinoate was prepared by the procedure of the previous example and melted with decomposition in the range 225°–240° C.

EXAMPLE 5

PREPARATION OF 4-DESACETYL-1-DESFORMYL VINCRISTINOIC ACID

A solution was prepared from 620 mg. of vincristine in 30 ml. of anhydrous ethanol to which had been added 55 ml. of 1 N aqueous sodium hydroxide. The solution was heated to refluxing temperature for one hour and then allowed to cool. The solution was extracted three times with methylenedichloride. The methylenedichloride extracts were combined, dried, and the methylenedichloride removed therefrom by evaporation. 4-Desacetyl-1-desformyl vincristinoic acid sodium salt thus obtained was a tan amorphous powder weighing 386 mg. Infrared spectrum showed a carbonyl band at 1735 cm.$^{-1}$ and no band at 1695 cm.$^{-1}$ showing an absence of the N-formyl group.

EXAMPLE 6

PREPARATION OF ETHYL 4-DESACETYL-1-DESFORMYL VINCRISTINOATE (23-ethyl-23-desmethyl-4-desacetyl-1-desformyl vincristine)

Following the procedure of Example 3, desacetyl desformyl vincristinoate acid as the sodium salt was esterified with ethanolic hydrogen chloride to yield ethyl 4-desacetyl-1-desformyl vincristinoate. The compound was obtained as a tan amorphous solid having an enhanced band in the infrared at 1735 cm.$^{-1}$ indicating increased number of ester groups present in the molecule. Mass spectrum analysis gave a molecular ion $m/e = 768$ consistent with the emperical formula C$_{44}$H$_{56}$N$_4$O$_8$.

EXAMPLE 7

PREPARATION OF ETHYL 4-DESACETYL VINCRISTINOATE

Ethyl 4-desacetyl-1-desformyl vincristinoate obtained in Example 6 was dissolved in 18 ml. of 97 percent formic acid to which 3 ml. of acetic anhydride had been added. The reaction mixture was allowed to stand under anhydrous conditions in the dark at ambient temperature for about four hours. The volatile constituents were then removed by evaporation, and the residue dissolved in water. The aqueous solution was made basic with 14 N ammonium hydroxide, and the basic layer extracted three times with methylene dichloride. The methylenedichloride extracts were combined and dried. Evaporation of the methylenedichloride yielded 106 mg. of a tan amorphous solid comprising ethyl 4-desacetyl vincristinoate formed in the above reaction. The compound was purified by chromatography over silica gel using ethanol as the eluant. Infrared spectrum of the compound showed strong bands of 1740 cm.$^{-1}$ (ester group) and at 1695 cm.$^{-1}$ (N-formyl) NMR spectrum of the compound was consistent with the postulated structure, and the molecular spectrum gave a molecular ion, $m/e = 796$ consistent with the empirical formula $C_{45}H_{56}N_4O_9$. The sulfate salt was prepared by the procedure of Example 3 and was a tan amorphous solid.

EXAMPLE 8

PREPARATION OF 2-HYDROXYETHYL 4-DESACETYL VINBLASTINOATE SULFATE

Following the procedure of Example 1 5 g. of vinblastine sulfate were converted to sodium 4-desacetyl vinblastinoate. The amorphous sodium salt was dissolved in ethylene glycol and this solution added to a solution of ethylene glycol saturated with hydrogen chloride at 0° C. The resulting reaction mixture was sealed in a flask and allowed to remain at ambient temperature for 16 hours. The reaction flask was then opened and 750 ml. of water added. 2-Hydroxyethyl 4-desacetyl vinblastinoate formed in the above procedure was isolated from the reaction mixture by the procedure of Example 3 for the preparation of the corresponding ethyl ester. The residual solid obtained contained 2-hydroxyethyl 4-desacetyl vinblastinoate was further purified by chromatography over silica gel using a 1:1 ethyl acetate-ethanol solvent mixture as the eluant. Fractions determined to contain the desired ester by thin layer chromatography were combined and the solvent evaporated therefrom. The sulfate salt of 2-hydroxyethyl 4-desacetyl vinblastinoate was prepared by the procedure of Example 3. The free base gave a molecular ion spectrum $m/e = 798$ consistent with the empirical formula $C_{45}H_{58}N_4O_9$.

EXAMPLE 9

PREPARATION OF 4-DESACETYL VINCRISTINE AND 1-DESFORMYL-4-DESACETYL VINCRISTINE

Two grams of 4-desacetyl vinblastine sulfate were dissolved in a mixture 230 ml. of acetone and 50 ml. of glacial acetic acid. A second solution prepared by dissolving 1 g. of chromium trioxide in 300 ml. of acetic anhydride and 30 ml. of glacial acetic acid containing a trace of water. The chromium trioxide solution was cooled to −60° C. The solution of the 4-desacetyl vinblastine sulfate was then added slowly to the cold chromium trioxide solution over a period of about 15 minutes. The reaction mixture was stirred vigorously for about 30 minutes at −60° C. 14 N ammonium hydroxide was then added slowly until the pH was 9.2. 1 l. of water was then added and the solution evacuated to remove acetone. The aqueous layer was extracted four times with methylene dichloride. The methylene dichloride extracts were combined, dried and the methylene dichloride evaporated in vacuo to leave a tan amorphous powder comprising a mixture of 4-desacetyl vincristine and 1-desformyl-4-desacetyl vincristine formed in the above reaction. The residue, a tan amorphous powder, was chromatographed over silica gel using a benzene-chloroform-triethyl amine (100-5-0-7.5) solvent mixture as the eluant. Fractions containing the vincristine derivatives, as determined by thin layer chromatography were combined and the solvent evaporated from them in vacuo. 130 mg. of 1-desformyl-4-desacetyl vincristine were obtained having the following physical characteristics: Infrared spectrum peak at 1730 cm$^{-1}$ (indicating an ester group). There was no peak corresponding to a formyl group. The infrared spectrum was identical with the infrared spectrum of 1-desformyl-4-desacetyl vincristine prepared from vincristine. Molecular ion spectrum/$m/e = 754,413,355,154$.

175 mg. of 4-desacetyl vincristine were obtained as a tan amorphous powder having the following physical data: Infrared spectrum peaks at 3560 cm$^{-1}$ (hydroxy) 1735 cm$^{-1}$ (ester group) 1690 cm$^{-1}$ (amide). The infrared spectrum was identical with that of 4-desacetyl vincristine prepared from vincristine. Molecular ion spectrum, $m/e = 782, 355, 154$. NMR δ 8.78 (CHO), 6.98 (aromatic hydrogen adjacent to N-formyl group) 6.78 (aromatic hydrogen meta to N-formyl group) 3.86 (aromatic methoxy group). Again, the NMR was identical with that found with desacetyl vincristine prepared from vincristine.

EXAMPLE 10

PREPARATION OF 2-CHLOROETHYL 4-DESACETYL VINBLASTINOATE

Following the procedure of Example 3, 4-desacetyl vinblastinoate acid sodium salt was esterified with 2-chloroethanol saturated with hydrogen chloride gas. The esterification mixture was allowed to stand in the dark at room temperature for three days whereupon the volatile constituents were removed in vacuo. The residual oil was dissolved in water and the acidic solution made basic with 14 M ammonium hydroxide. 2-Chloroethyl 4-desacetyl vinblastinoate being insoluble in the alkaline layer, separated and was extracted with dichloromethane. Three dichloromethane extracts were made and these were combined, dried and the solvent evaporated. The residual tan amorphous powder was chromatographed over silica gel using an ethyl acetate-ethanol (3:1) solvent mixture as the eluant. Fraction shown to contain 2-chloroethyl 4-desacetyl vinblastinoate by thin layer chromatography were combined. Evaporation of the solvent yielded a white amorphous powder having the following physical chemical data: Infrared absorption maxima at 1735 cm$^{-1}$. Molecular ion spectrum $m/e = 816,758,475,154$ consistency with $C_{45}H_{57}ClN_4O_8$. The sulfate salt was prepared as before.

I claim:
1. A compound of the formula

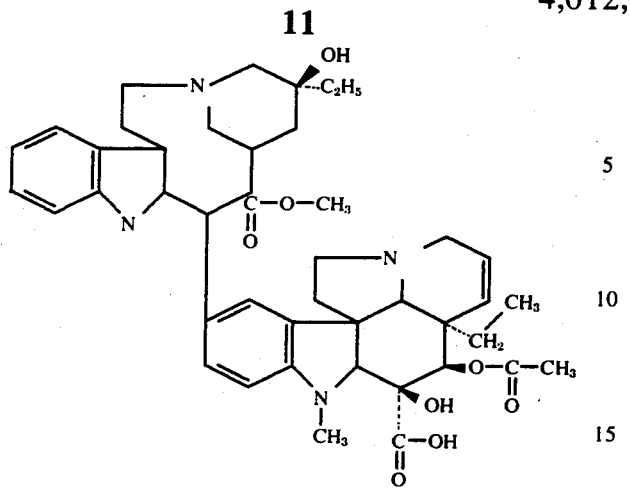
said compound being vinblastinoic acid.